United States Patent
Rebuffat et al.

(10) Patent No.: US 8,875,974 B2
(45) Date of Patent: Nov. 4, 2014

(54) STAPLER FOR MUCOSECTOMY

(71) Applicant: Covidien AG, Neuhausen am Rheinfall (CH)

(72) Inventors: Carlo Rebuffat, Carate Brianza MI (IT); Dante David, Cologno Monzese MI (IT)

(73) Assignee: Covidien AG (CH)

( * ) Notice: Subject to any disclaimer, the term of this patent is extended or adjusted under 35 U.S.C. 154(b) by 0 days.

(21) Appl. No.: 14/185,964

(22) Filed: Feb. 21, 2014

(65) Prior Publication Data

US 2014/0171985 A1 Jun. 19, 2014

Related U.S. Application Data

(63) Continuation of application No. 13/594,071, filed on Aug. 24, 2012, which is a continuation of application No. 12/529,909, filed as application No. PCT/IT2007/000166 on Mar. 7, 2007, now Pat. No. 8,272,555.

(51) Int. Cl.
*A61B 17/04* (2006.01)
*A61B 17/10* (2006.01)
*A61B 17/115* (2006.01)
*A61B 17/34* (2006.01)
*A61B 17/00* (2006.01)
*A61B 17/11* (2006.01)
*A61B 17/29* (2006.01)

(52) U.S. Cl.
CPC ......... *A61B 17/1155* (2013.01); *A61B 17/3423* (2013.01); *A61B 2017/00269* (2013.01); *A61B 17/115* (2013.01); *A61B 2017/1142* (2013.01); *A61B 2017/2901* (2013.01)
USPC ...................................... 227/177.1

(58) Field of Classification Search
USPC .............................. 227/175.1–182.1; 606/219
See application file for complete search history.

(56) References Cited

U.S. PATENT DOCUMENTS

| 295,798 A | 3/1884 | Pagett |
| 314,132 A | 3/1885 | Ingersoll |

(Continued)

FOREIGN PATENT DOCUMENTS

| CA | 908529 | 8/1972 |
| DE | 1057729 | 5/1959 |

(Continued)

OTHER PUBLICATIONS

PCT International Search Report for PCT/IT2007/000166 filed on Mar. 7, 2007 in the name of Carlo Rebuffat.

(Continued)

*Primary Examiner* — Robert Long

(57) ABSTRACT

The head of a stapler for mucosectomy comprises an external goblet-shaped body (1) wherein an internal goblet-shaped body (2) is concentrically and slidingly located, at the edge of which a circular blade (3) is fixed. The internal goblet-shaped body (2) is provided with a central hole (5) wherein a rod (6) is slidingly inserted, at the end (7) of which an anvil (8; 8') is fixed. One or more annular grooves (11), which are parallel and suitably spaced one from the other, are formed on the lateral surface of the rod (6) perpendicularly to the axis thereof. Said grooves (11) are intended to receive a portion of mucosa (9a) which is included in a purse string suture as the mucosa is tied around the rod (6). By retracting the rod (6) in the central hole (5) of the stem (2a) of the internal goblet-shaped body (2) the mucosa to be removed is carried into the internal goblet-shaped body (2). The anvil (8; 8') and the circular blade (3) are moved closer one to the other, by suitable means, in order to cut the tissues when the stapler is in a closed position.

12 Claims, 3 Drawing Sheets

(56) References Cited

U.S. PATENT DOCUMENTS

| | | | |
|---|---|---|---|
| 357,216 A | 2/1887 | McCall | |
| 2,469,880 A | 5/1949 | Kowan | |
| 2,769,441 A | 11/1956 | Abramson | |
| 2,922,415 A | 1/1960 | Campagna | |
| 3,193,165 A | 7/1965 | Akhalaya et al. | |
| 3,388,847 A | 6/1968 | Kasulin et al. | |
| 3,552,626 A | 1/1971 | Astafiev | |
| 3,638,652 A | 2/1972 | Kelley | |
| 3,701,347 A | 10/1972 | Belkin | |
| 3,771,526 A | 11/1973 | Rudie | |
| 4,198,982 A | 4/1980 | Fortner et al. | |
| 4,207,898 A | 6/1980 | Becht | |
| 4,289,133 A | 9/1981 | Rothfuss | |
| 4,304,236 A | 12/1981 | Conta et al. | |
| 4,319,576 A | 3/1982 | Rothfuss | |
| 4,350,160 A | 9/1982 | Kolesov et al. | |
| 4,351,466 A | 9/1982 | Noiles | |
| 4,379,457 A | 4/1983 | Gravener et al. | |
| 4,473,077 A | 9/1984 | Noiles et al. | |
| 4,476,863 A * | 10/1984 | Kanshin et al. | 606/153 |
| 4,485,817 A | 12/1984 | Swiggett | |
| 4,488,523 A | 12/1984 | Shichman | |
| 4,505,272 A | 3/1985 | Utyamyshev et al. | |
| 4,505,414 A | 3/1985 | Filipi | |
| 4,520,817 A | 6/1985 | Green | |
| 4,550,870 A | 11/1985 | Krumme et al. | |
| 4,573,468 A | 3/1986 | Conta et al. | |
| 4,576,167 A | 3/1986 | Noiles | |
| 4,592,354 A * | 6/1986 | Rothfuss | 227/179.1 |
| 4,603,693 A | 8/1986 | Conta et al. | |
| 4,606,343 A | 8/1986 | Conta et al. | |
| 4,646,745 A | 3/1987 | Noiles | |
| 4,665,917 A * | 5/1987 | Clanton et al. | 606/153 |
| 4,667,673 A | 5/1987 | Li | |
| 4,671,445 A | 6/1987 | Barker et al. | |
| 4,700,703 A | 10/1987 | Resnick et al. | |
| 4,703,887 A * | 11/1987 | Clanton et al. | 227/19 |
| 4,708,141 A | 11/1987 | Inoue et al. | |
| 4,717,063 A | 1/1988 | Ebihara | |
| 4,752,024 A | 6/1988 | Green et al. | |
| 4,754,909 A | 7/1988 | Barker et al. | |
| 4,776,506 A | 10/1988 | Green | |
| 4,817,847 A | 4/1989 | Redtenbacher et al. | |
| 4,834,067 A | 5/1989 | Block | |
| 4,873,977 A | 10/1989 | Avant et al. | |
| 4,893,622 A | 1/1990 | Green et al. | |
| 4,903,697 A | 2/1990 | Resnick et al. | |
| 4,907,591 A | 3/1990 | Vasconcellos et al. | |
| 4,917,114 A | 4/1990 | Green et al. | |
| 4,957,499 A | 9/1990 | Lipatov et al. | |
| 4,962,877 A | 10/1990 | Hervas | |
| 5,005,749 A | 4/1991 | Aranyi | |
| 5,042,707 A | 8/1991 | Taheri | |
| 5,047,039 A | 9/1991 | Avant et al. | |
| 5,104,025 A | 4/1992 | Main et al. | |
| 5,119,983 A | 6/1992 | Green et al. | |
| 5,122,149 A | 6/1992 | Broome | |
| 5,122,156 A | 6/1992 | Granger et al. | |
| 5,139,513 A | 8/1992 | Segato | |
| 5,158,222 A | 10/1992 | Green et al. | |
| 5,188,638 A | 2/1993 | Tzakis | |
| 5,193,731 A | 3/1993 | Aranyi | |
| 5,197,648 A | 3/1993 | Gingold | |
| 5,197,649 A | 3/1993 | Bessler et al. | |
| 5,205,459 A | 4/1993 | Brinkerhoff et al. | |
| 5,221,036 A | 6/1993 | Takase | |
| 5,222,963 A | 6/1993 | Brinkerhoff et al. | |
| 5,253,793 A | 10/1993 | Green et al. | |
| 5,256,149 A | 10/1993 | Banik et al. | |
| 5,258,016 A * | 11/1993 | DiPoto et al. | 606/232 |
| 5,261,920 A * | 11/1993 | Main et al. | 606/153 |
| 5,271,543 A | 12/1993 | Grant et al. | |
| 5,271,544 A | 12/1993 | Fox et al. | |
| 5,275,322 A | 1/1994 | Brinkerhoff et al. | |
| 5,282,810 A | 2/1994 | Allen et al. | |
| 5,285,944 A | 2/1994 | Green et al. | |
| 5,285,945 A | 2/1994 | Brinkerhoff et al. | |
| 5,292,053 A | 3/1994 | Bilotti et al. | |
| 5,309,927 A | 5/1994 | Welch | |
| 5,312,024 A | 5/1994 | Grant et al. | |
| 5,314,435 A | 5/1994 | Green et al. | |
| 5,314,436 A | 5/1994 | Wilk | |
| 5,330,486 A | 7/1994 | Wilk | |
| 5,333,773 A | 8/1994 | Main et al. | |
| 5,344,059 A | 9/1994 | Green et al. | |
| 5,346,115 A | 9/1994 | Perouse et al. | |
| 5,348,259 A | 9/1994 | Bianco et al. | |
| 5,350,104 A | 9/1994 | Main et al. | |
| 5,351,674 A | 10/1994 | Hawks | |
| 5,355,897 A | 10/1994 | Pietrafitta et al. | |
| 5,360,154 A | 11/1994 | Green | |
| 5,368,215 A | 11/1994 | Green et al. | |
| D353,197 S | 12/1994 | Hawks | |
| 5,392,979 A | 2/1995 | Green et al. | |
| 5,395,030 A | 3/1995 | Kuramoto et al. | |
| 5,403,333 A | 4/1995 | Kaster et al. | |
| 5,404,870 A | 4/1995 | Brinkerhoff et al. | |
| 5,411,508 A | 5/1995 | Bessler et al. | |
| 5,425,736 A | 6/1995 | Wadworth | |
| 5,425,738 A | 6/1995 | Gustafson et al. | |
| D360,261 S | 7/1995 | Swanson et al. | |
| 5,433,721 A | 7/1995 | Hooven et al. | |
| 5,437,684 A | 8/1995 | Calabrese et al. | |
| 5,439,156 A | 8/1995 | Grant et al. | |
| 5,443,198 A | 8/1995 | Viola et al. | |
| 5,447,514 A | 9/1995 | Gerry et al. | |
| 5,454,825 A | 10/1995 | Van Leeuwen et al. | |
| 5,464,412 A | 11/1995 | Budding | |
| 5,464,415 A | 11/1995 | Chen | |
| 5,470,006 A | 11/1995 | Rodak | |
| 5,474,223 A | 12/1995 | Viola et al. | |
| 5,497,934 A | 3/1996 | Brady et al. | |
| 5,503,635 A | 4/1996 | Sauer et al. | |
| 5,509,893 A | 4/1996 | Pracas | |
| 5,522,534 A | 6/1996 | Viola et al. | |
| 5,533,661 A | 7/1996 | Main et al. | |
| 5,588,579 A | 12/1996 | Schnut et al. | |
| 5,609,285 A | 3/1997 | Grant et al. | |
| 5,626,591 A | 5/1997 | Kockerling et al. | |
| 5,632,433 A | 5/1997 | Grant et al. | |
| 5,639,008 A | 6/1997 | Gallagher et al. | |
| 5,641,111 A | 6/1997 | Ahrens et al. | |
| 5,658,300 A | 8/1997 | Bito et al. | |
| 5,658,312 A | 8/1997 | Green et al. | |
| D384,412 S | 9/1997 | Mainiero | |
| 5,669,918 A | 9/1997 | Balazs et al. | |
| 5,685,474 A | 11/1997 | Seeber | |
| 5,709,335 A | 1/1998 | Heck | |
| 5,715,987 A | 2/1998 | Kelley et al. | |
| 5,718,360 A | 2/1998 | Green et al. | |
| 5,720,755 A | 2/1998 | Dakov | |
| 5,732,872 A | 3/1998 | Bolduc et al. | |
| 5,741,273 A | 4/1998 | O'Regan | |
| 5,749,896 A | 5/1998 | Cook | |
| 5,758,814 A | 6/1998 | Gallagher et al. | |
| 5,799,857 A | 9/1998 | Robertson et al. | |
| 5,814,055 A | 9/1998 | Knodel et al. | |
| 5,833,698 A | 11/1998 | Hinchliffe et al. | |
| 5,836,503 A | 11/1998 | Ehrenfels et al. | |
| 5,839,639 A | 11/1998 | Sauer et al. | |
| 5,855,312 A | 1/1999 | Toledano | |
| 5,860,581 A | 1/1999 | Robertson et al. | |
| 5,868,760 A | 2/1999 | McGuckin, Jr. | |
| 5,881,943 A | 3/1999 | Heck et al. | |
| 5,915,616 A | 6/1999 | Viola et al. | |
| 5,916,150 A | 6/1999 | Sillman | |
| 5,931,776 A | 8/1999 | Dotolo | |
| 5,947,363 A | 9/1999 | Bolduc et al. | |
| 5,951,576 A | 9/1999 | Wakabayashi | |
| 5,957,363 A | 9/1999 | Heck | |
| 5,957,902 A | 9/1999 | Teves | |
| 5,993,468 A | 11/1999 | Rygaard | |
| 6,024,748 A | 2/2000 | Manzo et al. | |
| 6,050,472 A | 4/2000 | Shibata | |

(56) References Cited

U.S. PATENT DOCUMENTS

| | | |
|---|---|---|
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,126,594 A | 10/2000 | Bayer |
| 6,136,009 A | 10/2000 | Mears |
| 6,142,933 A | 11/2000 | Longo et al. |
| 6,149,667 A | 11/2000 | Hovland et al. |
| 6,152,936 A | 11/2000 | Christy et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balázs et al. |
| 6,264,086 B1 | 7/2001 | McGuckin, Jr. |
| 6,269,997 B1 | 8/2001 | Balázs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,315,713 B1 | 11/2001 | Takada |
| 6,338,737 B1 | 1/2002 | Toledano |
| 6,343,731 B1 | 2/2002 | Adams et al. |
| 6,364,852 B1 | 4/2002 | Lee |
| 6,387,105 B1 | 5/2002 | Gifford, III et al. |
| 6,398,795 B1 | 6/2002 | McAlister et al. |
| 6,402,008 B1 | 6/2002 | Lucas |
| 6,428,473 B1 | 8/2002 | Leonard et al. |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,497,654 B1 | 12/2002 | Leonard et al. |
| 6,503,192 B1 | 1/2003 | Ouchi |
| 6,503,259 B2 | 1/2003 | Huxel et al. |
| 6,503,912 B1 | 1/2003 | Wagner et al. |
| 6,506,157 B1 | 1/2003 | Teigman et al. |
| 6,517,566 B1 | 2/2003 | Hovland et al. |
| 6,520,398 B2 | 2/2003 | Nicolo |
| 6,533,157 B1 | 3/2003 | Whitman |
| 6,547,798 B1 | 4/2003 | Yoon et al. |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,616,603 B1 | 9/2003 | Fontana |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,702,741 B2 | 3/2004 | Rioux et al. |
| 6,716,222 B2 | 4/2004 | McAlister et al. |
| 6,716,233 B1 | 4/2004 | Whitman |
| 6,726,697 B2 | 4/2004 | Nicholas et al. |
| 6,740,098 B2 | 5/2004 | Abrams et al. |
| 6,740,101 B2 | 5/2004 | Houser et al. |
| 6,742,692 B2 | 6/2004 | Hartwick |
| 6,743,244 B2 | 6/2004 | Blatter et al. |
| 6,761,687 B1 | 7/2004 | Doshi et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2* | 11/2005 | Heinrich ..................... 227/175.1 |
| 6,978,922 B2 | 12/2005 | Bilotti et al. |
| 6,981,941 B2 | 1/2006 | Whitman et al. |
| 7,029,438 B2 | 4/2006 | Morin et al. |
| 7,032,798 B2 | 4/2006 | Whitman et al. |
| 7,037,314 B2 | 5/2006 | Armstrong |
| 7,059,331 B2 | 6/2006 | Adams et al. |
| 7,059,510 B2 | 6/2006 | Orban, III |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2* | 11/2006 | Abrams et al. ................ 606/115 |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,229,428 B2 | 6/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,303,106 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| D564,657 S | 3/2008 | Tsai |
| 7,364,060 B2 | 4/2008 | Milliman |
| 7,398,908 B2 | 7/2008 | Holsten et al. |
| 7,399,305 B2 | 7/2008 | Csiky et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,452,329 B2 | 11/2008 | Bastia et al. |
| 7,455,676 B2 | 11/2008 | Holsten et al. |
| 7,455,682 B2 | 11/2008 | Viola |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |

(56) References Cited

U.S. PATENT DOCUMENTS

| | | |
|---|---|---|
| 7,588,174 B2 | 9/2009 | Holsten et al. |
| 7,600,663 B2 | 10/2009 | Green |
| 7,611,038 B2 | 11/2009 | Racenet et al. |
| 7,611,458 B2 | 11/2009 | Sias |
| 7,635,385 B2 | 12/2009 | Milliman et al. |
| 7,666,198 B2 * | 2/2010 | Suyker et al. .................. 606/153 |
| 7,708,759 B2 | 5/2010 | Lubbers et al. |
| 7,789,848 B2 | 9/2010 | Gannoe et al. |
| 7,918,869 B2 | 4/2011 | Saadat et al. |
| 7,975,895 B2 | 7/2011 | Milliman |
| 8,011,554 B2 | 9/2011 | Milliman |
| 2001/0000903 A1 | 5/2001 | Heck et al. |
| 2001/0010320 A1 | 8/2001 | Bolduc et al. |
| 2001/0054636 A1 | 12/2001 | Nicolo |
| 2002/0020732 A1 | 2/2002 | Adams et al. |
| 2002/0047036 A1 | 4/2002 | Sullivan et al. |
| 2002/0063143 A1 | 5/2002 | Adams et al. |
| 2002/0185516 A1 | 12/2002 | Heck et al. |
| 2002/0185517 A1 | 12/2002 | Vresh et al. |
| 2003/0019905 A1 | 1/2003 | Adams et al. |
| 2003/0047582 A1 | 3/2003 | Sonnenschein et al. |
| 2003/0057251 A1 | 3/2003 | Hartwick |
| 2003/0065342 A1 | 4/2003 | Nobis et al. |
| 2003/0069472 A1 | 4/2003 | Butler |
| 2003/0073981 A1 | 4/2003 | Whitman et al. |
| 2003/0089757 A1 | 5/2003 | Whitman |
| 2003/0111507 A1 | 6/2003 | Nunez |
| 2003/0127491 A1 | 7/2003 | Adams et al. |
| 2003/0130559 A1 | 7/2003 | Morin et al. |
| 2003/0132267 A1 | 7/2003 | Adams et al. |
| 2003/0144675 A1 | 7/2003 | Nicolo |
| 2003/0178465 A1 | 9/2003 | Bilotti et al. |
| 2003/0183671 A1 | 10/2003 | Mooradian et al. |
| 2003/0192936 A1 | 10/2003 | Hartwick |
| 2003/0192937 A1 | 10/2003 | Sullivan et al. |
| 2003/0201301 A1 | 10/2003 | Bolduc et al. |
| 2003/0218047 A1 | 11/2003 | Sharma et al. |
| 2003/0222117 A1 | 12/2003 | Orban, III |
| 2004/0092960 A1 | 5/2004 | Abrams et al. |
| 2004/0092974 A1 | 5/2004 | Gannoe et al. |
| 2004/0118896 A1 | 6/2004 | Sharma et al. |
| 2004/0134964 A1 | 7/2004 | Adams et al. |
| 2004/0153124 A1 | 8/2004 | Whitman |
| 2004/0232198 A1 | 11/2004 | Adams et al. |
| 2004/0254590 A1 | 12/2004 | Hoffman et al. |
| 2004/0260152 A1 | 12/2004 | Sant et al. |
| 2005/0051597 A1 | 3/2005 | Tolendano |
| 2005/0067454 A1 | 3/2005 | Vresh et al. |
| 2005/0087580 A1 | 4/2005 | Orban, III |
| 2005/0107813 A1 | 5/2005 | Gilete Garcia |
| 2005/0116009 A1 | 6/2005 | Milliman |
| 2005/0125009 A1 | 6/2005 | Perry et al. |
| 2005/0143758 A1 | 6/2005 | Abbott et al. |
| 2005/0145674 A1 | 7/2005 | Sonnenschein et al. |
| 2005/0145675 A1 | 7/2005 | Hartwick et al. |
| 2005/0203527 A1 | 9/2005 | Carrison et al. |
| 2005/0277811 A1 | 12/2005 | Richards et al. |
| 2006/0000869 A1 | 1/2006 | Fontayne |
| 2006/0009797 A1 | 1/2006 | Armstrong |
| 2006/0011698 A1 | 1/2006 | Okada et al. |
| 2006/0036129 A1 | 2/2006 | Sias |
| 2006/0047307 A1 | 3/2006 | Ortiz et al. |
| 2006/0047308 A1 | 3/2006 | Ortiz et al. |
| 2006/0085032 A1 | 4/2006 | Viola |
| 2006/0085033 A1 | 4/2006 | Criscuolo et al. |
| 2006/0085034 A1 | 4/2006 | Bettuchi |
| 2006/0085035 A1 | 4/2006 | Viola |
| 2006/0097025 A1 | 5/2006 | Milliman et al. |
| 2006/0108393 A1 | 5/2006 | Heinrich et al. |
| 2006/0144897 A1 | 7/2006 | Jankowski et al. |
| 2006/0151567 A1 | 7/2006 | Roy |
| 2006/0191975 A1 | 8/2006 | Adams et al. |
| 2006/0201989 A1 | 9/2006 | Ojeda |
| 2006/0201993 A1 | 9/2006 | Hur |
| 2006/0212046 A1 | 9/2006 | Pearce et al. |
| 2006/0241692 A1 | 10/2006 | McGuckin et al. |
| 2006/0255090 A1 | 11/2006 | Milliman et al. |
| 2006/0289601 A1 | 12/2006 | Orban, III |
| 2007/0023475 A1 | 2/2007 | Csiky |
| 2007/0029363 A1 | 2/2007 | Popov |
| 2007/0034666 A1 | 2/2007 | Holsten et al. |
| 2007/0034668 A1 | 2/2007 | Holsten et al. |
| 2007/0038248 A1 | 2/2007 | Heinrch |
| 2007/0043264 A1 | 2/2007 | Gillis et al. |
| 2007/0060952 A1 | 3/2007 | Roby et al. |
| 2008/0091218 A1 | 4/2008 | Richardson |
| 2008/0097478 A1 | 4/2008 | Doughty et al. |
| 2008/0249566 A1 | 10/2008 | Harris et al. |
| 2008/0262511 A1 | 10/2008 | Delaney |
| 2009/0212088 A1 | 8/2009 | Okada et al. |
| 2009/0230170 A1 | 9/2009 | Milliman |
| 2009/0236388 A1 | 9/2009 | Cole et al. |
| 2009/0236389 A1 | 9/2009 | Cole et al. |
| 2009/0236390 A1 | 9/2009 | Cole et al. |
| 2009/0236391 A1 | 9/2009 | Cole et al. |
| 2009/0236392 A1 | 9/2009 | Cole et al. |
| 2009/0236394 A1 | 9/2009 | Cole et al. |
| 2009/0236396 A1 | 9/2009 | Cole et al. |
| 2009/0236397 A1 | 9/2009 | Cole et al. |
| 2009/0236398 A1 | 9/2009 | Cole et al. |
| 2009/0236400 A1 | 9/2009 | Cole et al. |
| 2009/0236401 A1 | 9/2009 | Cole et al. |
| 2009/0242612 A1 | 10/2009 | Adams et al. |
| 2009/0250502 A1 | 10/2009 | Milliman |
| 2009/0255976 A1 | 10/2009 | Marczyk et al. |
| 2009/0302089 A1 | 12/2009 | Harari et al. |
| 2009/0321496 A1 | 12/2009 | Holsten et al. |
| 2010/0001036 A1 | 1/2010 | Marczyk et al. |
| 2010/0001037 A1 | 1/2010 | Racenet et al. |
| 2010/0019016 A1 | 1/2010 | Edoga et al. |
| 2010/0025452 A1 | 2/2010 | Whitman |
| 2010/0038401 A1 | 2/2010 | Milliman et al. |
| 2010/0051668 A1 | 3/2010 | Milliman et al. |
| 2010/0059571 A1 | 3/2010 | Chen et al. |
| 2010/0065607 A1 | 3/2010 | Orban, III et al. |
| 2010/0065609 A1 | 3/2010 | Schwemberger |
| 2010/0084453 A1 | 4/2010 | Hu |
| 2010/0089971 A1 | 4/2010 | Milliman et al. |
| 2010/0108741 A1 * | 5/2010 | Hessler et al. .............. 227/179.1 |
| 2010/0301098 A1 | 12/2010 | Kostrzewski |
| 2011/0006102 A1 | 1/2011 | Kostrzewski |
| 2011/0006104 A1 * | 1/2011 | Felix .......................... 227/179.1 |
| 2011/0282381 A1 | 11/2011 | Cronin et al. |
| 2011/0282382 A1 | 11/2011 | McAlister et al. |

FOREIGN PATENT DOCUMENTS

| | | |
|---|---|---|
| DE | 3301713 | 11/1989 |
| EP | 0152382 | 8/1985 |
| EP | 0173451 | 3/1986 |
| EP | 0190022 | 8/1986 |
| EP | 282157 | 9/1988 |
| EP | 0503689 | 9/1992 |
| FR | 1461464 | 12/1966 |
| FR | 1588250 | 4/1970 |
| FR | 2443239 | 12/1979 |
| GB | 1185292 | 3/1970 |
| GB | 2016991 | 9/1979 |
| GB | 2070499 | 9/1981 |
| NL | 7711347 | 10/1977 |
| SU | 995765 | 2/1983 |
| SU | 1509052 A1 | 1/1988 |
| WO | WO 8706448 | 11/1987 |
| WO | WO 8900406 | 1/1989 |
| WO | WO 9006085 | 6/1990 |

OTHER PUBLICATIONS

PCT International Search Report for PCT/IT2005/000619 filed Oct. 26, 2005 in the name of Carlo Rebuffat, et al.

Canadian Office Action dated Apr. 8, 2013.

* cited by examiner

STAPLER FOR MUCOSECTOMY

This application is a continuation of U.S. patent application Ser. No. 13/594,071, filed on Aug. 24, 2012, which is a continuation of U.S. patent application Ser. No. 12/529,909, filed on Feb. 22, 2010, now U.S. Pat. No. 8,272,555, which is a National Stage Entry under 35 U.S.C. §371(a) of International Patent Application No. PCT/IT2007/000166, filed on Mar. 7, 2007. The entire content of each of the applications identified above is incorporated by reference herein.

The present invention relates to a stapler for mucosectomy in hollow organs and, more particularly, a type of stapler which is provided with a central grooved rod allowing to carry out a precise mucosectomy of a larger volume of mucosal tissue.

Mucosectomy is an operation which is particularly suited for the treatment of haemorrhoids, rectocele and rectal mucosal prolapse. Circular mechanical staplers are already known, both for applying staples and for applying compression devices such as e.g. fragmentable rings. Said staplers are provided with a central shaft. The objective of mucosectomy is to remove a portion of mucosa which is as large as possible, so as to ensure a remarkable "lifting" of the mucosa of the hollow organ.

In order to achieve this objective, in U.S. Pat. No. 6,102,271 a circular stapler is disclosed whose head comprises two concentric goblet-shaped bodies. Two through openings are provided on the lateral surface of said goblet-shaped bodies, in the proximity of the stems thereof. The through openings allow the purse-string suture thread to pass outwards therethrough. The suture thread can thus be pulled towards the outside of the above mentioned goblet-shaped bodies so as to drag into the inside thereof a volume of mucosa which is as large as possible. The mucosa is then cut by a circular blade which is fixed to the edge of the internal goblet-shaped body. At the same time, a shaft which is centrally arranged relative to the goblet-shaped bodies moves an anvil which is fixed to the end of the shaft in the proximity of the edge of the external goblet-shaped body for applying suture staples. However, the stapler described in the above mentioned patent has the drawback that the manual pulling of the suture threads during the step of closing the stapler does not allow to remove the mucosa in a homogeneous and controlled way with exactness.

Object of the present invention is thus to provide a stapler for mucosectomy which is free from such drawbacks. Said object is achieved by a stapler whose main characteristics are specified in the first claim, while other characteristics are specified in the subsequent claims.

In order to achieve said object, the stapler according to the present invention is provided with a central rod having one or more annular grooves formed on its lateral surface crosswise to its axis. Such grooves are intended to receive a portion of tissue when a purse-string suture is tied around the rod, as well as to prevent said portion of tissue from undesirably sliding along the central rod as the latter is retracted inside the stem of the internal goblet-shaped body. In order to ensure that during said retraction of the rod the hollow body wall is dragged in a controlled and homogeneous way into the internal goblet-shaped body, said grooves are suitably dimensioned and exactly spaced one from the other.

Another advantage provided by the stapler according to the present invention is to allow a precise removal of different amounts of mucosa simply by selecting a certain annular groove among those formed and calibrated on the rod of the stapler.

Further advantages and characteristics of the stapler according to the present invention will be evident to those skilled in the art from the following detailed and non-limiting disclosure of two embodiments thereof with reference to the annexed drawings wherein.

Figure 1:
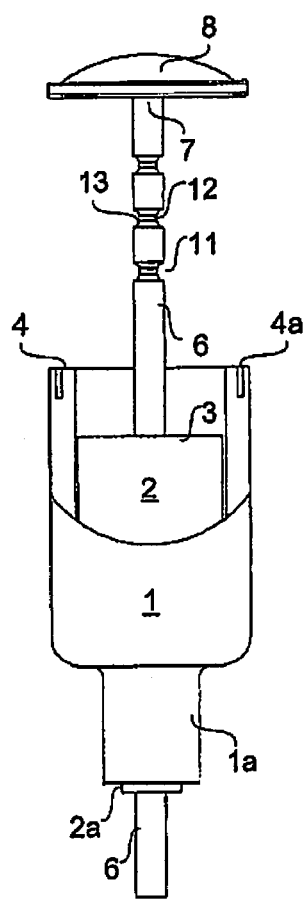
FIG. 1 is a partially sectioned side view of the head of a first embodiment of the stapler according to the present invention in an open position.
Figure 2:
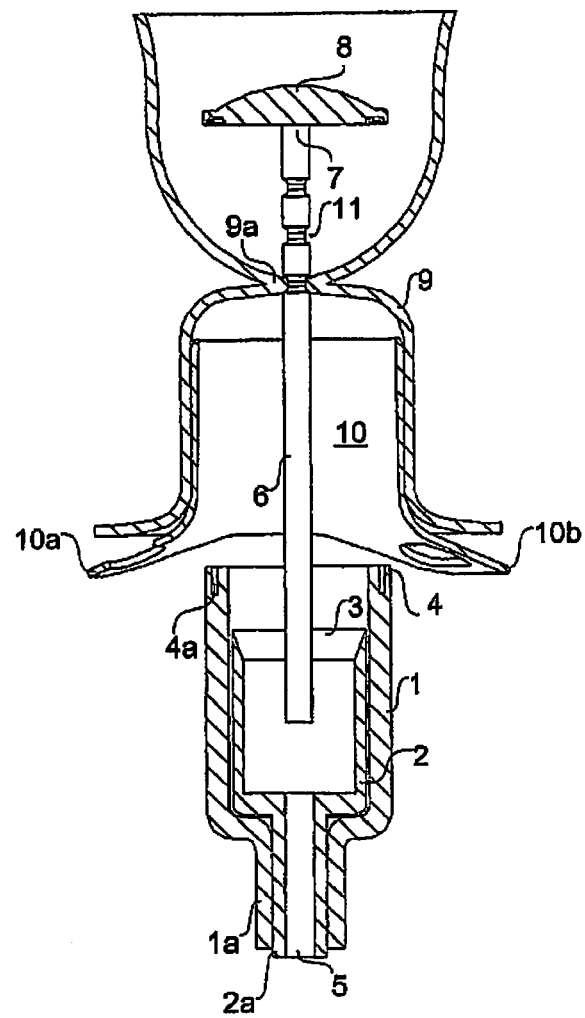
FIG. 2 is a longitudinally sectioned view of the head of the stapler in FIG. 1 being introduced inside a partially sectioned hollow organ through a hollow cylindrical introducer.

FIGS. 1 and 2 show a head of a stapler comprising in a known way an external goblet-shaped body 1, being provided with a first hollow stem 1a, wherein a smaller internal goblet-shaped body 2 is concentrically and slidingly provided. A circular blade 3 is fixed to the edge of said internal goblet-shaped body 2. In a retracted position of the internal goblet-shaped body 2, the circular blade 3 is located inside the external goblet-shaped body 1 without protruding from the edge 4 of the latter. At the opposite side with respect to the circular blade 3 the internal goblet-shaped body 2 has a second hollow stem 2a which is provided with a central hole 5 wherein a rod 6 is slidingly inserted. In correspondence to the part which is opposite to the one where the central hole 5, wherein the anvil rod 6 slides, is located, the anvil rod 6 has an end 7 to which an anvil 8 is fixed. The hollow stem 1a of the external goblet-shaped body 1 of the head of the stapler shown in the drawings is connected in a known way to a handle (not shown). Said anvil 8 and said circular blade 3 are intended to be progressively moved closer one to the other in order to cut the mucosa as the stapler head reach a closed position, that is when the anvil rod 6 is progressively retracted into the central hole 5 of the second hollow stem 2a by means of suitable rod retraction means (not shown in the drawings) which are included in the stapler handle, as it is known to a person skilled in the art. The circular blade 3 is moved forward by suitable blade moving means (not shown in the drawings) which are also included in the stapler handle, as it is known to a person skilled in the art. The edge 4 of the internal goblet-shaped body 2 can be provided with suitable recesses 4a which are designed to contain suitable suture means, such as for example metallic staples. In FIG. 2 the stapler head is shown in the open position and introduced in a hollow organ 9 through a hollow cylindrical introducer 10 being provided with flanges 10a and 10b.

The rod 6 has, according to the invention, one or more annular grooves 11 which are spaced one from the other and formed on the lateral surface of the rod 6 perpendicularly to the axis thereof. Said annular grooves 11 are intended to receive in their inside a portion of mucosa 9a of the hollow organ 9 which is included in a purse string suture (not shown) when the mucosa 9a is tied around the rod 6. The number of annular grooves 11 and the distance between them are suitably calibrated in order to provide a plurality of fixing positions for the purse-string suture on the rod so as to be always able remove an amount of mucosa which is as large as possible.

The depth of the annular grooves 11 of the rod 6 is comprised between 0.5 mm and 3 mm, preferably it is about 1 mm. The cross-section of the rod 6 is preferably circular, but it can also be polygonal.

Each annular groove 11 of the rod 6 consists of a cylindrical surface 12, which has a smaller diameter than the rest of the lateral surface of the rod 6 and is connected thereto by a fillet surface 13. The radius of the fillet surface 13 between the cylindrical surface 12 and the rest of the lateral surface of the rod 6 is preferably about 1 mm.

In order to carry out the mucosectomy with the stapler according to the present invention, first a purse string suture is made in a prolapsing portion of mucosa 9a to be removed from a hollow organ 9. The stapler head is then introduced in the hollow organ 9 in the open position, that is with the anvil 8 being spaced from the edge 4 of the external goblet-shaped body 1, by making the anvil 8 pass through the purse string suture. Subsequently the purse string suture is tied around the rod 6 between the edge 4 of the external goblet-shaped body 1 and the anvil 8. In particular the purse string suture is tied around the rod 6 in correspondence to an annular groove 11 which is formed on the rod 6 in such a way that the portion of mucosa 9a being included by the purse string suture is laid therein without any possibility to slide along the rod 6. In order to remove in a controlled, homogeneous and exact way large amounts of mucosa, a determined annular groove 11 is selected among the annular grooves 11 formed on the rod 6 at a well calibrated reciprocal distance.

Figures 3, 4:
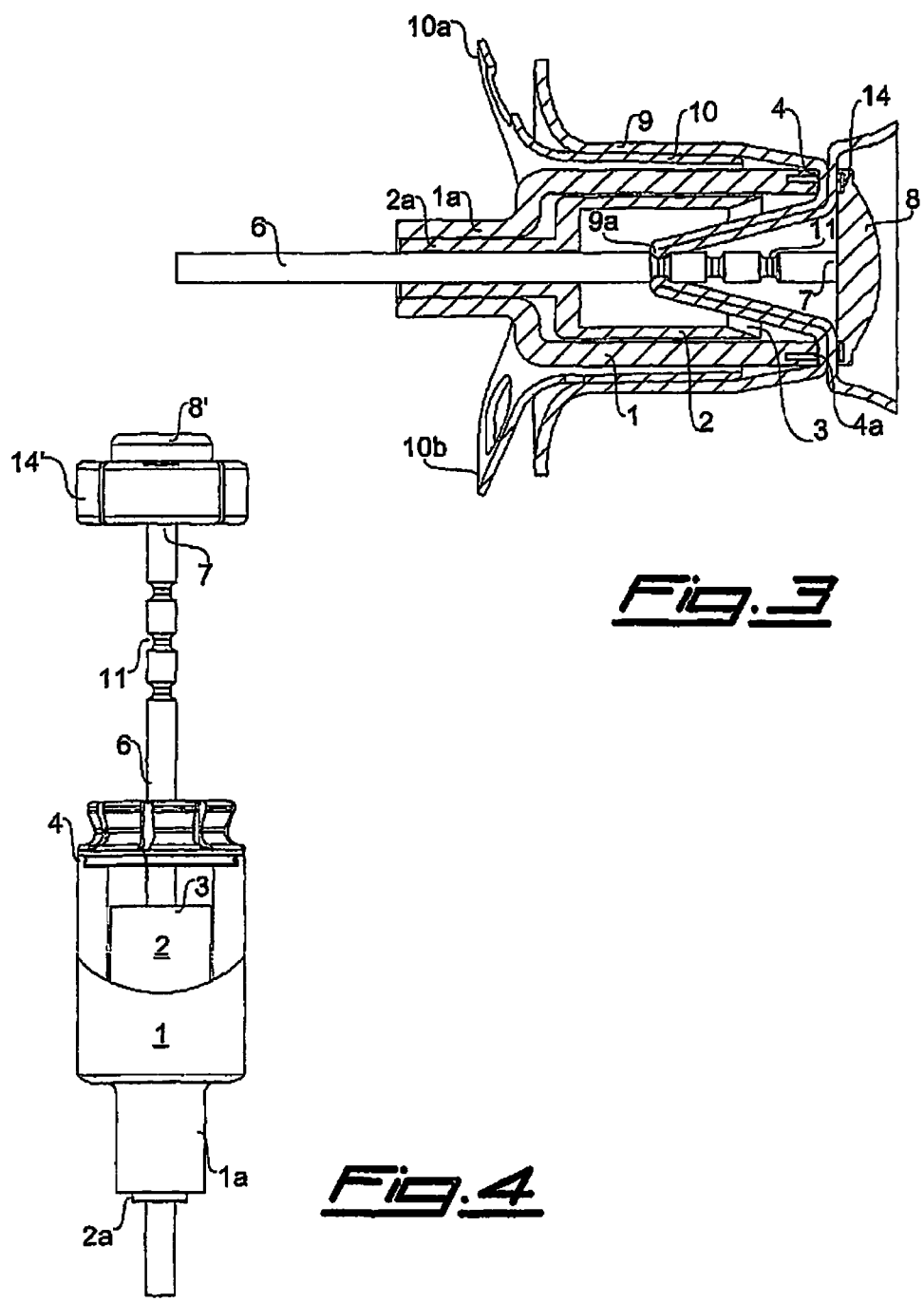
FIG. 3 is a longitudinally sectioned view of the head of the stapler in a closed position inside a hollow organ through a hollow cylindrical introducer.
FIG. 4 is a partially sectioned side view of the head of a second embodiment of the stapler according to the present invention in an open position.

As it is shown in FIG. 3, the stapler head is finally closed by retracting the rod 6 in the central hole 5 of the stem 2a of the internal goblet-shaped body 2, thus carrying the mucosa to be removed into the internal goblet-shaped body 2 and contemporaneously causing the anvil 8 to push the mucosa to be removed against the edge 4 of the external goblet-shaped body 1.

After closing the stapler head by suitable rod retraction means, suture means 14 are applied to the mucosa of the hollow body 9 in correspondence to the edge 4 of the external goblet-shaped body 1. For example, such suture means 14 can be metallic staples. Subsequently, the internal goblet-shaped body 2 and the circular blade 3 being integral thereto are moved towards the anvil 8, by suitable moving means, thus separating the mucosa contained in the internal goblet-shaped body 2 from the mucosa of the hollow organ 9 to which the suture means 14 have been applied. Finally, the stapler head is extracted from the hollow organ 9.

Figure 5:
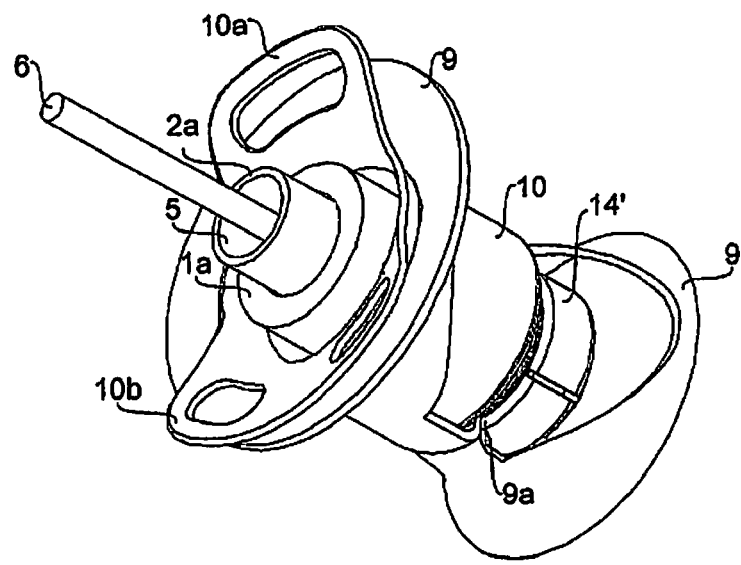
FIG. 5 is an axonometric view of the head of the stapler of FIG. 4 in a closed position being introduced inside a partially sectioned hollow organ through a hollow cylindrical introducer.
Figure 6:
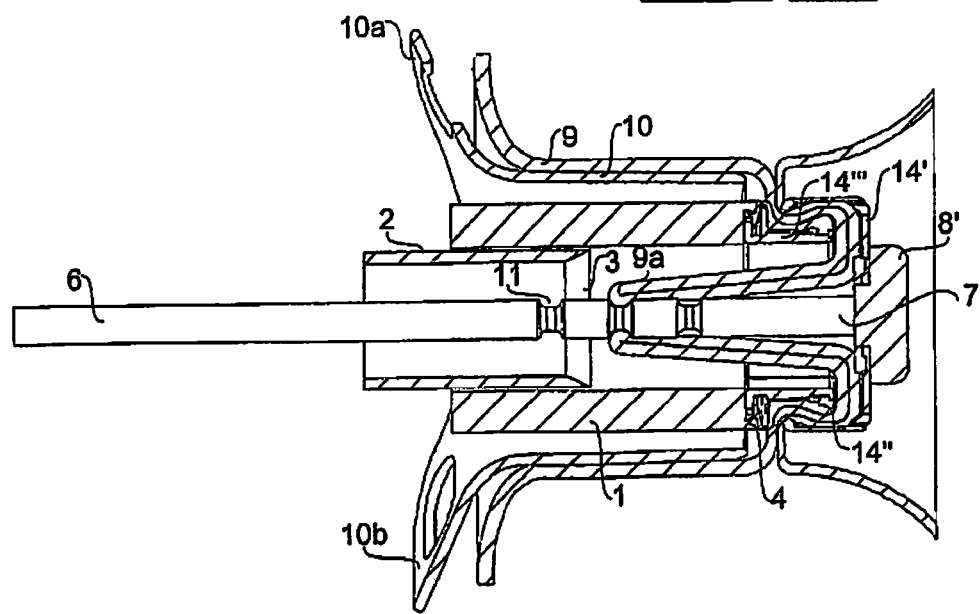
FIG. 6 is a longitudinally sectioned view of the head of the stapler of FIG. 5.

FIGS. 4, 5 and 6 show a second alternative embodiment wherein the stapler head is suitable to apply a fragmentable compression device. In this embodiment the anvil 8' is a support for a component 14' of the compression device to be coupled to complementary components 14", 14''', which are arranged in correspondence to the edge 4 of the external goblet-shaped body 1, when the stapler head is closed, as it is known to a person skilled in the art.

Preferably, during the mucosectomy the hollow body 9 is held open by means of a hollow cylindrical introducer 10, as it is shown in the FIGS. 2, 3, 5 and 6.

In order to illustrate the usefulness of the presence on the rod 6 of several annular grooves 11 and to highlight the biunivocal correspondence which is thus created between the distance of each individual groove 11 from the anvil 8, 8' and the volume of mucosa to be removed, reference is made to the following non-limiting example of a stapler according to the present invention.

In a stapler provided with a circular blade 3 having a diameter of 24 mm and with a rod 6 having a diameter equal to 5 mm, 1 mm-deep annular grooves 11 are formed on the rod 6 thus, in correspondence to the grooves 11, the rod 6 has a diameter of 3 mm.

If an annular groove 11 was located in correspondence to the connecting point of the rod 6 to the anvil 8, 8', when a purse string suture is tied around the rod 6 in correspondence to said groove 11, 21 mm of mucosa might be removed, that is two times the distance between the circular blade 3 and the annular groove 11, said distance being equal to the radius of 12 mm of the circular blade 3 minus the 1.5 mm radius of the rod 6 in correspondence to the groove 11.

In order to remove larger amounts of mucosa, it is preferable that the stapler is provided with three annular grooves 11 arranged at 10 mm, 20 mm and 30 mm respectively from the anvil 8, 8'. Such grooves correspond to about 29 mm, 45 mm and 63.5 mm of mucosa which can be removed. In fact, grooves 11 which are spaced from the anvil 8, 8', when the rod 6 is retracted in the stem 2a of the goblet-shaped body 2, allow to drag into said goblet-shaped body 2 a larger amount of mucosa, as the distance between the circular blade 3 and the annular groove 11 wherein the mucosa 9a is fixed by means of the purse string suture increases, as it is shown in FIGS. 3 and 6. It is evident that the surgeon using the stapler according to the present invention can operate more rapidly, exactly and safely due to the present invention.

The invention claimed is:

1. A method of performing a surgical procedure, comprising:
   securing a flexible member to a section of target tissue;
   securing the flexible member to a groove formed in a portion of an anvil member;
   drawing the portion of the anvil member to which the flexible member is secured into a head assembly of a surgical fastener applying apparatus to draw a portion of the target tissue into the head assembly; and
   firing the surgical fastener applying apparatus to eject one or more surgical fasteners from a body of the surgical fastener applying apparatus through the target tissue into the anvil member to secure the one or more surgical fasteners to the target tissue.

2. The method of claim 1, wherein securing the flexible member includes securing the flexible member to a rod of the anvil member, the groove being formed in the rod.

3. The method of claim 2, wherein securing the flexible member includes securing the flexible member directly to the rod.

4. The method of claim 1, further comprising inserting the anvil member into an opening in a patient.

5. The method of claim 2, wherein securing the flexible member to the groove includes selecting the groove from a plurality of grooves formed in the anvil member.

6. The method of claim 5, wherein selecting the groove includes selecting one of three grooves formed in the anvil member.

7. The method of claim 6, wherein securing the flexible member to the groove includes securing the flexible member to the selected groove.

8. The method of claim 6, wherein securing the flexible member to the groove includes securing the flexible member to the anvil member such that the flexible member is secured to the rod 10 mm from an anvil supported on a distal end of the rod.

9. The method of claim 6, wherein securing the flexible member includes securing the flexible member to the anvil member such that the flexible member is secured to the rod 20 mm from an anvil supported on a distal end of the rod.

10. The method of claim 6, wherein securing the flexible member includes securing the flexible member to the anvil member such that the flexible member is secured to the rod 30 mm from an anvil supported on a distal end of the rod.

11. The method of claim 1, wherein drawing the portion of the anvil member to which the flexible member is secured into the head assembly includes approximating the anvil member and the head assembly to compress the target tissue therebweteen.

12. The method of claim 11, wherein firing the surgical fastener applying apparatus includes advancing a blade member distally to sever the target tissue.

\* \* \* \* \*